United States Patent [19]

Pursell

[11] 4,279,362
[45] Jul. 21, 1981

[54] DISPENSING OF HYGIENIC FLUIDS

[76] Inventor: Grant W. Pursell, R.D. 1, Box 69C, Pittstown, N.J. 08867

[21] Appl. No.: 6,688

[22] Filed: Jan. 26, 1979

[51] Int. Cl.³ .......................... A61M 7/02; B65D 35/22
[52] U.S. Cl. ..................................... 222/94; 128/229; 128/251; 222/136; 222/399
[58] Field of Search ............... 222/94, 95, 136, 386.5, 222/389, 399; 128/251, 229; 141/2, 3, 25

[56] References Cited

U.S. PATENT DOCUMENTS

| 964,730 | 7/1910 | Ackerman | 128/229 |
|---|---|---|---|
| 967,450 | 8/1910 | Holes | 222/95 X |
| 1,473,979 | 11/1923 | Simmons | 128/229 |
| 2,571,424 | 10/1951 | Dailey | 128/229 UX |
| 2,751,127 | 6/1956 | Mitton | 222/386.5 |
| 2,758,747 | 8/1956 | Stevens | 222/386.5 X |
| 2,849,256 | 8/1958 | Kowal | 128/229 X |
| 3,104,664 | 9/1963 | Ladd | 128/229 |
| 3,521,792 | 7/1970 | Davidson | 222/136 |
| 3,533,409 | 10/1970 | Greer | 128/251 X |

Primary Examiner—F. J. Bartuska
Attorney, Agent, or Firm—George E. Kersey

[57] ABSTRACT

Hygienic fluids, such as soap, water for rinsing, and douching liquids are dispensed using a hand-holdable water powered multi-purpose device. The device includes separate compartments for soap and douching concentrate which are activated by a water supply line upon operation of appropriate valving. The dispenser permits simple and rapid cleaning of selected portions of the body when time and conditions do not permit general bathing.

13 Claims, 3 Drawing Figures

DISPENSING OF HYGIENIC FLUIDS

BACKGROUND OF THE INVENTION

This invention relates to the dispensing of hygienic fluids, and more particularly, to the efficient dispensing of such fluids.

As a matter of personal hygiene it is often important to cleanse portions of the body when time and conditions do not permit overall bathing. For that purpose it is common to use either a hand held syringe or a container which provides gravity fed desired cleansing ingredients through a hand manipulatable outlet which can be directed to specified parts of the body. These prior art techniques are slow and cumbersome.

In the case of a hand-held syringe, it is necessary to change the syringe fluid each time there is a change in sanitizing conditions. Moreover, it is not possible to obtain a clear rinse unless the device is charged and discharged with the rinse over many operating cycles. In the case of the gravity fed pouches, it is again necessary to change fluids when there is a change in sanitizing conditions. Thus to effect a rinse or to change a mix it is necessary to clean the pouch, rinse it, and substitute a different liquid. Moreover, the foregoing techniques are restricted in their utility and efficiency.

Accordingly, it is an object of the invention to facilitate the dispensing of hygienic fluids. Another object is to provide for the simple and efficient dispensing of a multiplicity of different kinds of fluids.

Still another object of the invention is to increase the rate at which the desired dispensing can be made and to exercise effective control over the rate of dispensing.

A further object of the invention is the need for eliminating hand operated syringes and gravity fed pouches in order to provide the pressure necessary for dispensing of hygienic fluids.

A further object of the invention is to eliminate the need for rinsing and replenishing the contents of a pouch or syringe at periodic intervals.

SUMMARY OF THE INVENTION

In accomplishing the foregoing and related objects, the invention provides dispensing one or more hygienic fluids by applying fluid pressure to a device, using the fluid pressure to exert pressure on a collapsible sack containing a prescribed hygienic fluid, and releasing the hygienic fluid from the sack. The hygienic fluid in the sack can be mixed with the pressure applying fluid, where, for example, water pressure is applied to a sack containing a douche concentrate which is then mixed with the outgoing stream of water to provide a desired douching solution without the need for, and disadvantage of, a gravity fed pouch or syringe.

In accordance with one aspect of the invention, a water powered dispenser is provided which can be adapted for ordinary cleansing as well as for douching. For that purpose the dispenser includes a plurality of different compartments, each containing a collapsible storage sack that can be subjected to water pressure from an ordinary faucet connection. Thus a rinsing valve can be operated to provide an adequate and continuous supply of rinse water while simultaneously providing for dispensing of selected hygienic fluids, as desired by the user.

In accordance with another aspect of the invention, the dispenser is arranged to prevent the inadvertently dispensing of a hygienic fluid, such as douching liquid, before the device has been connected to a water supply.

In accordance with a further aspect of the invention, the dispenser is a multi-purpose hygienic device which is convenient to hold and operate. It can be used in conjunction with the ordinary toilet found in bathrooms, thus providing the equivalent of a bidet without requiring the cost and space of that facility.

DESCRIPTION OF THE DRAWINGS

Other aspects of the invention will become apparent after considering several illustrative embodiments taken in conjunction with the drawings in which.

DETAILED DESCRIPTION

Figure 1:
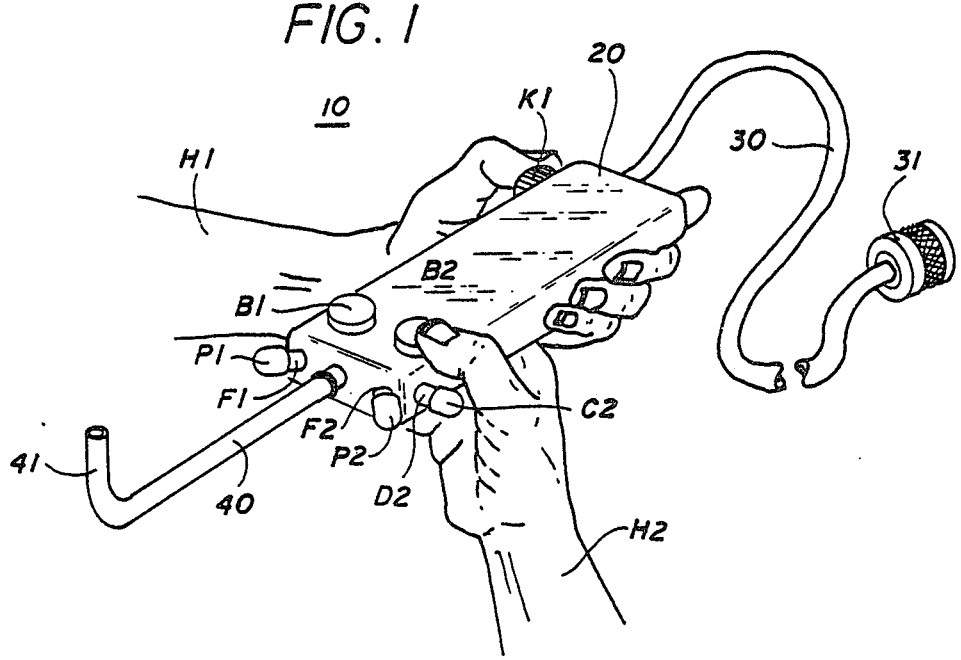
FIG. 1 is a perspective view of a hygienic dispenser in accordance with the invention.

Turning to the drawings, a sanitary dispenser 10 in accordance with the invention is shown being used by being held in the hands H1 and H2 of a user. The dispenser 10 includes a multi-compartment container 20 which is operated from a water source through an inlet tube 30. The inlet tube 30 can be affixed, for example, to an ordinary faucet outlet using a threaded cap 31, or any other faucet accessory (not shown). The output from the container 20 is by way of a changeable outlet tube 40 which is intended for rinsing for the particular embodiment of FIG. 1.

The flow of water from the inlet tube 30 through the multi-compartment container 20 and out of the outlet tube 40 is controlled by a water rinse control knob K1. In addition the container contains separate controls B1 and B2 for the dispensing of selected fluids, for example, a liquid douching fluid and liquid soap. When the water inlet 30 is connected, and the associated water tap is "on", liquid soap can be dispensed from the dispenser nozzle D2 (when the protective cap C2 has been removed) by depressing the control button B2. Liquid soap is then squirted into the palm of the Hand H2 as long as the button B2 is depressed. On the other hand, when the control knob K1 is rotated, water will flow through the unit 20, out of the outlet 40, for rinsing, when the particular tube of FIG. 1 is used. In addition, once the knob has been rotated to its "on" position, the hand H1 can be moved to allow depression of the control button B1 to cause the output from the tube to be mixed with a selected substance that has been preloaded through the filler F1.

Figure 2:
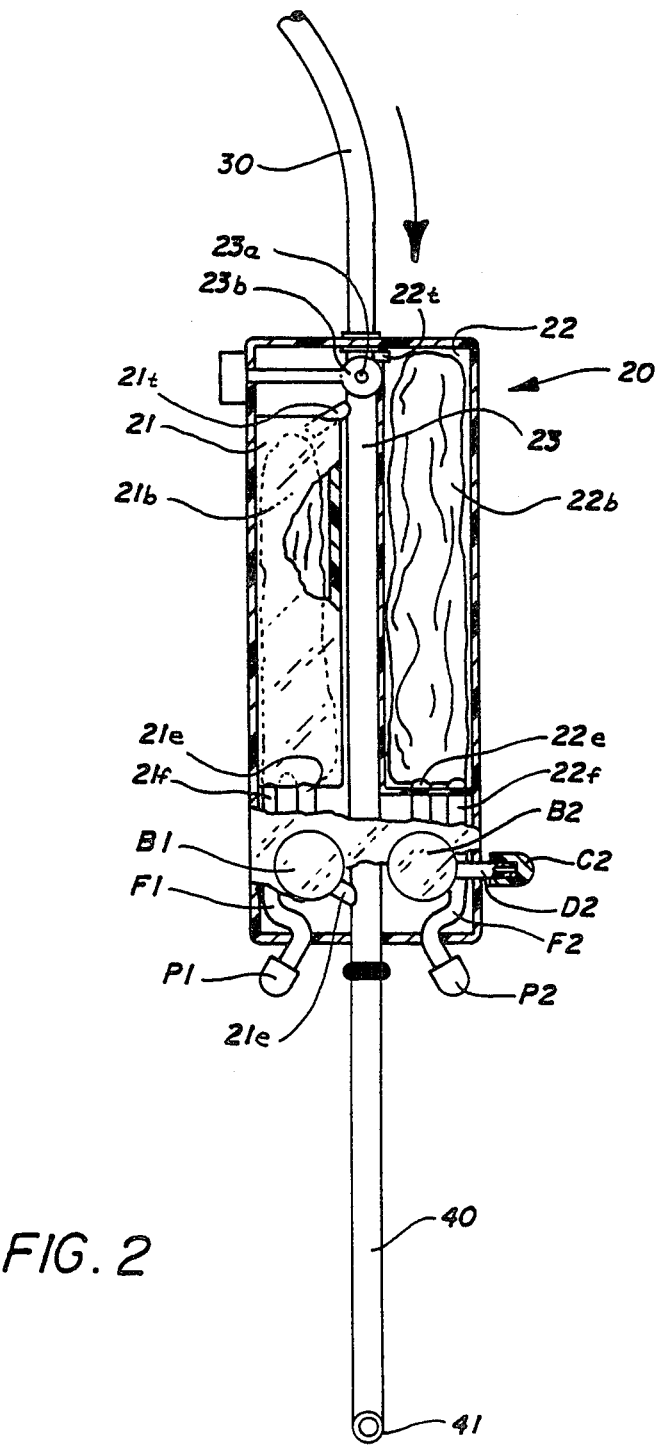
FIG. 2 is a sectional view of the dispenser of FIG. 1 illustrating the multi-compartmental use of storage sacks for use in the controllable dispensing of prescribed hygienic fluids.

The structural arrangement for the dispensing device 20 is set forth in the sectional view of FIG. 2. The container 20 includes a through-passage 23 which is connected to a water supply tube 30 at one end and to the outlet tube 40 at the other end. The through-passage 23 may be changed to be adapted to a wide variety of inlet and outlet situations. As shown in FIG. 2 the container 20 has two internal compartments 21 and 22 for respective fluids to be dispensed. The left-hand compartment 21 includes a collapsible bag 21b that can be filled with any liquid concentrate that is desired to be mixed with water passing along through-passage 23. Similarly the right-hand compartment 22 contains a collapsible bag 22b that can be filled with liquid to be dispensed, such as liquid soap. The force exerted against the fluids in the bags 21b and 22b comes from the water supply source. For that purpose a compartment inlet 22t allows water pressure to be appled directly to the bag 22b whenever there is water pressure in the inlet tube 30. In the case of the other bag 21b, however, there is no pressure until the water rinse knob K1 has been operated.

In the particular embodiment of FIG. 2 the water rinse knob K1 extends to a ball stop valve 23b in the main cylindrical line 23 of the container 22. When the knob K1 is rotated 90° an opening 23a in the ball stop permits water to flow in the line 23 and apply pressure to the bag 21b through an inlet line 21t. This permits the concentrate within the bag 21b to be fed into the main line 23 through the exit tube 21e when the control button B1 is depressed. It will be understood that the control typified by the buttons B1 and B2 may be exerced in a wide variety of standard ways.

Figure 3:
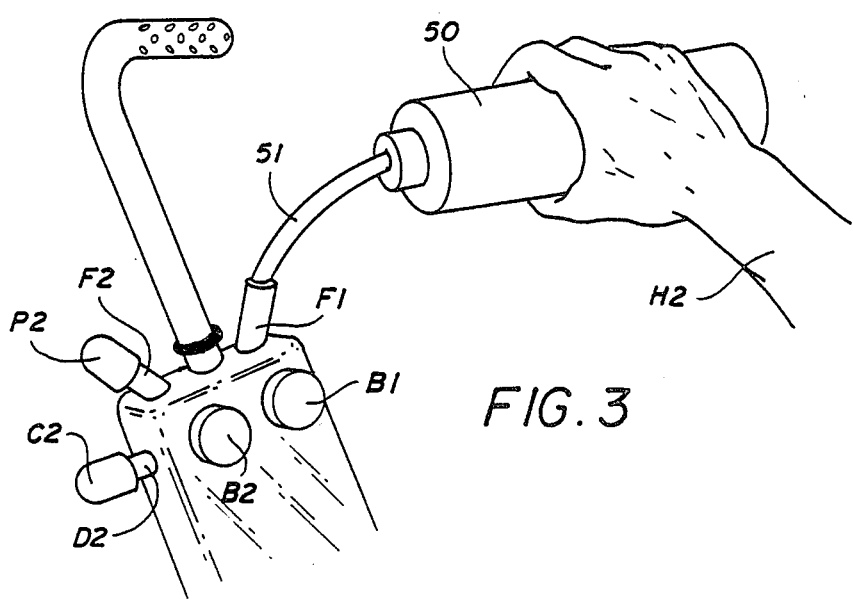
FIG. 3 is a perspective view of the dispenser of FIG. 1 with an alternative dispenser attachment and illustrating the filling of one of the storage sacks in one of the compartments of the dispenser.

The dispenser 10 in accordance with the invention can be adapted to regular douching by replacing the rinsing outlet 40 of FIG. 1 with a douching outlet 40' of conventional form as indicated in FIG. 3. To fill the douche sack 21b (FIG. 2) the protective cap P1 is removed and the nozzle 51 of a concentrate is inserted into the filler tube F1. The body of container 50 is then squeezed with the hand H2, where desired. Standard valving may be employed with the filling operation and the container 50 may be pressured so that the concentrate will enter the sack spontaneously.

The dispenser 10 is usable in a wide variety of ways. In particular it allows the user to wash and rinse desired areas of the body while seated on a toilet. In the case of a female user it can be used to provide a hygienic douche in place of a bidet, again while seated on a toilet.

For washing, the user first fills the soap dispenser portion 22b of the device 10 with a liquid soap. The hose 30 is then connected to a bathroom faucet and the hot/cold water mixture adjusted to the desired temperature by operating the control knob K1. While desirably seated on the toilet, the user places the device 10 in his left hand H1, with his left thumb and index finger in position to operate the water rinse control knob K1 as shown in FIG. 1. The right hand H2 holds the lower portion of the device 10 to help guide the water rinse outlet tube 40 into the toilet between the legs. The water rinse control K1 is operated to effect the desired rinsing. The water release control K1 is returned to its non-operating position, the cap C2 is removed and the soap dispenser button B2 is depressed with the right thumb. This releases liquid soap from the soap dispenser tube D2 into the cupped right hand. When soaping is completed the water rinse control K1 is again operated.

For douching the user replaces the water rinse adapter tube 40 with a douching adaptor tube 40' (FIG. 3). The douche dispenser portion 21b of the device 10 is filled with liquid douching concentrate. The hose 30 is connected to the bathroom faucet and the hot/cold water mixture again is adjusted to the desired temperature. While seated on the toilet, the user applies the tube 40' in the usual way and depresses the douche dispenser button B1 with the water rinse control K1 in its "on" position. This causes the water and douching concentrate to mix automatically. Since the douche dispenser button B1 will not operate if depressed alone, accidental discharge of douching solution in concentrated form is prevented.

It is to be noted that the water rinse tube 40 is bent with its tip 41 at approximately 90° to best accomplish rinsing. The douching tube 40' also has a tip 41' which is angled at approximately 90°. The tip 41' has a closed end and a standard apertured length.

While the particular embodiment of FIG. 2 illustrates a ball-type closure valve 23b, it will be understood that a wide variety of other rinse control valves may be used as well, such as a spring loaded depressible button.

In addition, although the storage members 21b and 22b are collapsible sacks, it will be understood that the collapsible members may employ moveable barriers or take the form of cylinders with pistons against which the fluid pressure is exerted. When the hose 30 is disconnected from the faucet, the pressure on the barrier is released, thus allowing the user to refill the compartments 21b and 22b with their respective liquids.

While various aspects of the invention have been set forth by the drawings and specification, it is to be understood that the foregoing detailed description is for illustration only and that various changes in parts, as well as the substitution of equivalent constituents for those shown and described may be made without departing from the spirit and scope of the invention as set forth in the appended claims.

What is claimed is:

1. A dispenser comprising a container including at least two separate compartments, each containing a storage member
    means for applying fluid pressure to the storage members comprising a conduit extending into, through and out of said container, said container having an inlet into each of said compartments, an outlet, and means for controlling the pressure applied to each storage member comprising a valve positioned in said fluid applying conduit between the inlets of said compartments;
    whereby fluid pressure is fully applied to the storage member in one of the compartments and is applied to the storage member in another of said compartments according to the extent of the position of said valve which further controls the amount of fluid discharged at the outlet of said conduit.

2. Apparatus as defined in claim 1 further including means for refilling said storage member while said fluid pressure is applied thereto.

3. Apparatus as defined in claim 1 wherein said container has a plurality of separate compartments, each containing a collapsible storage member, and means are provided for applying different pressures simultaneously to the collapsible storage members.

4. Apparatus as defined in claim 1 wherein the contents of said storage member are releasable into the pressure applying fluid and means are included for controlling the amount of mixing that takes place between the portion of the contents released from said storage member and said pressure applying fluid.

5. A hygienic dispenser in accordance with claim 1 wherein one of said compartments contains a douching concentrate and the other of said compartments contains soap, and the pressure applying fluid is water.

6. A hygienic dispenser in accordance with claim 1 wherein the outlet of said conduit includes a bent outlet tube.

7. A hygienic dispenser in accordance with claim 6 wherein said outlet tube has a substantially linear rigid portion that extends to a tip disposed at an angle of about 90 degrees with respect to said linear portion;

thereby to provide a hygienic dispenser which facilitates simple and rapid cleansing of selected portions of the body.

8. A hygienic dispenser in accordance with claim 1 wherein the contents of said compartments are subject to push-button release.

9. A hygienic dispenser in accordance with claim 1 wherein a release is provided for the other compartment which is inoperative until said fluid pressure is applied to said other compartment.

10. A hygienic dispenser in accordance with claim 1 wherein the output of the other compartment converges with the fluid in said conduit.

11. A hygienic disperser comprising a container including at least two separate compartments, each containing a collapsible storage member,
- means for applying fluid pressure to the collapsible storage members comprising a conduit extending into, through, and out of said container, said conduit having an inlet into each of said compartments,
- a rigid, elongated outlet tube which has a tip that is disposed at an angle with respect to the elongation of said tube, and
- means for controlling the pressure applied to each collapsible storage member comprising a valve positioned in said fluid applying conduit between the inlets of said compartments;
- whereby fluid pressure is fully applied to the collapsible storage member in one of the compartments and is applied to the collapsible storage member in another of said compartments according to the extent of the opening of said valve which further controls the amount of fluid discharged at the outlet of said conduit in a hygienic dispenser which facilitates simple and rapid cleansing of selected portions of the body.

12. Apparatus as defined in claim 11 further including an outlet from said first collapsible storage member into said conduit beyond the position of said valve; an outlet from said second collapsible storage member beyond the position of said valve; a pressurizable filling port connected to said first collapsible storage member; and a pressurizable filling port connected to said second collapsible storage member.

13. Apparatus as defined in claim 11 wherein said valve comprises a ball stop having an opening extending therethrough, which when positioned at an angle of 90° with respect to the axis of said conduit blocks the flow of said fluid therethrough, but permits a controlled amount of said fluid to flow through said conduit as said ball stop is rotated from the 90° position.

* * * * *